(12) United States Patent
Talton et al.

(10) Patent No.: US 7,846,459 B2
(45) Date of Patent: Dec. 7, 2010

(54) METHODS FOR PREPARING COMPOSITIONS FOR REPAIRING BONE

(75) Inventors: James D. Talton, Alachua, FL (US); James F. Kirk, Del Mar, CA (US)

(73) Assignee: Nanotherapeutics, Inc., Alachua, FL (US)

( * ) Notice: Subject to any disclaimer, the term of this patent is extended or adjusted under 35 U.S.C. 154(b) by 700 days.

(21) Appl. No.: 11/777,001

(22) Filed: Jul. 12, 2007

(65) Prior Publication Data

US 2008/0014279 A1 Jan. 17, 2008

Related U.S. Application Data

(62) Division of application No. 11/070,413, filed on Mar. 2, 2005.

(60) Provisional application No. 60/548,945, filed on Mar. 2, 2004.

(51) Int. Cl.
*A61K 9/00* (2006.01)
*A61K 9/14* (2006.01)
*A61K 9/16* (2006.01)

(52) U.S. Cl. .................. 424/400; 424/422; 424/489; 424/490; 424/492; 435/325

(58) Field of Classification Search ............. 424/400, 424/422, 489, 490, 492; 435/325
See application file for complete search history.

(56) References Cited

U.S. PATENT DOCUMENTS

| | | | |
|---|---|---|---|
| 4,191,747 | A | 3/1980 | Scheicher |
| 4,352,884 | A | 10/1982 | Nakashima et al. |
| 4,938,763 | A | 7/1990 | Dunn et al. |
| 5,035,896 | A | 7/1991 | Apfel et al. |
| 5,324,519 | A | 6/1994 | Dunn et al. |
| 5,650,108 | A | 7/1997 | Nies et al. |
| 5,702,716 | A | 12/1997 | Dunn et al. |
| 5,744,153 | A | 4/1998 | Yewey et al. |
| 5,990,194 | A | 11/1999 | Dunn et al. |
| 6,030,635 | A | 2/2000 | Gertzman et al. |
| 6,311,690 | B1 | 11/2001 | Jefferies |
| 6,773,714 | B2 | 8/2004 | Dunn et al. |
| 7,122,057 | B2 | 10/2006 | Beam et al. |
| 2001/0014831 | A1* | 8/2001 | Scarborough ............ 623/23.51 |
| 2001/0016703 | A1 | 8/2001 | Wironen et al. |
| 2001/0037091 | A1 | 11/2001 | Wironen et al. |
| 2002/0018796 | A1 | 2/2002 | Wironen |
| 2002/0076429 | A1 | 6/2002 | Wironen et al. |
| 2002/0098222 | A1 | 7/2002 | Wironen et al. |
| 2003/0180262 | A1 | 9/2003 | Wironen et al. |
| 2003/0206937 | A1 | 11/2003 | Gertzman et al. |

FOREIGN PATENT DOCUMENTS

| | | |
|---|---|---|
| DE | 41 26 800 | 2/1993 |
| EP | 0 041 614 | 12/1981 |
| EP | 0 581 387 | 2/1994 |
| WO | WO 90/01955 | 3/1990 |
| WO | WO 91/02811 | 3/1991 |
| WO | WO 03/090717 | 11/2003 |
| WO | WO 2005/084725 | 9/2005 |

OTHER PUBLICATIONS

Examination Report dated Oct. 31, 2007, in European Patent Application No. 05724174.7.
Office Action dated Nov. 23, 2007, issued in co-pending U.S. Appl. No. 11/070,413.
U.S. Appl. No. 11/070,413, Compositions for Repairing Bone and Methods for Preparing and Using Such Compositions, filed Mar. 2, 2005.
U.S. Appl. No. 11/776,997, Methods of Repairing Bone, filed Jul. 12, 2007.
Department of Health & Human Services, Food and Drug Administration, 510(k) No. K062459 Summary and Letter (2007).
Department of Health and Human Services, Agency for Toxic Substances and Disease Registry, Public Health Statement, Barium CAS#: 7440-39-3:1-6 (2005).
English Language Derwent Abstract for DE 41 26 800, Sep. 8, 1991.

(Continued)

*Primary Examiner*—Ruth A Davis
(74) *Attorney, Agent, or Firm*—Finnegan, Henderson, Farabow, Garrett & Dunner, LLP

(57) ABSTRACT

This invention relates to an improved method of preparing an implantable gel or paste for placement between injured bones or placement in bony voids to induce regeneration, and the compositions produced thereby. Specifically, mineral, ceramic, or processed bone particles are coated with a high molecular weight polymer capable of forming a viscous gel when reconstituted with water, saline, autologous blood, sera, or other medically acceptable solution. This high molecular weight polymer coating material may be a natural or synthetic polymeric material, producing a wettable gel upon exposure to water, saline, or another solution. In storage, the composition will be granular and dry but easily wetted. In use, the material is reconstituted to a viscous malleable paste by the simple addition of water or other medically acceptable solution without the need for aggressive mixing. The paste may be delivered by syringe or manually deposited yet will be resistant to lavage or to displacement by gravity induced flow.

24 Claims, 5 Drawing Sheets

OTHER PUBLICATIONS

Examination Report dated Mar. 1, 2007, in European Patent Application No. 05724174.7.

Graphs with Gel Forming Quality of Gelatin, Great Lakes Geletin, Greyslake, IL, 2007.

International Search Report for Application No. PCT/US2005/006579 dated Aug. 26, 2005, Ex. R. Menidjel.

Office Action dated May 29, 2007, in co-pending U.S. Appl. No. 11/070,413.

Response to Examination Report dated Mar. 1, 2007, in European Patent Application No. 05724174.7, filed with the European Patent Office on Aug. 13, 2007.

Sabokbar et al., *J. Bone Joint Surg.* 79-B:129-137 (1997).

Wimhurst et al., *J. Bone Joint Surg.*, 83-B:588-592 (2001).

* cited by examiner

METHODS FOR PREPARING COMPOSITIONS FOR REPAIRING BONE

This is a divisional of application Ser. No. 11/070,413, filed Mar. 2, 2005 which claims the benefit of U.S. Provisional Application No. 60/548,945, filed Mar. 2, 2004, both of which are incorporated herein by reference.

BACKGROUND OF THE INVENTION

A. Government Interests

None

B. Related Applications

The present application claims priority under 35 U.S.C. §119 to U.S. Provisional Patent Application Ser. No. 60/548, 945, filed Mar. 2, 2004. The entire contents of the aforementioned application are specifically incorporated herein by reference in its entirety.

C. Field of the Invention

This invention relates to an improved method of preparing an implantable paste for placement between injured bones or placement in bony voids to induce regeneration, and the compositions produced thereby. Specifically, mineral, ceramic, or processed bone particles, so-called bioactive particles (BP), are coated with a matrix material (MM) capable of forming a viscous gel when reconstituted with water, saline, autologous blood, sera, or other medically acceptable solution. This MM may be a natural or synthetic polymeric material, producing a wettable paste upon exposure to water, saline, or another aqueous solution. In storage, the composition will be granular and dry, but easily wetted during reconstitution. To prepare the composition for administration, the material is reconstituted to a viscous malleable paste by the simple addition of water or other medically acceptable solution without the need for aggressive mixing. The paste may be delivered by syringe or manually deposited yet will be resistant to lavage or to displacement by gravity induced flow.

D. Description of Related Art

Bone pastes, such as REGENAFIL™ or OSTEOFIL™ produced by Regeneration Technologies, Inc., comprise particles of allograft demineralized bone matrix (DBM) and gelatin (U.S. Patent Applications 20020098222, 20020018796, and 20020076429). As taught by Scheicher (U.S. Pat. No. 4,191,747), suspending osteoinductive and/or osteoconductive materials in gelatin solutions provides an implantable composition with temperature dependant flow properties. Above the gel transition temperature, the composition is free flowing while below that temperature, i.e. when at body temperature, it forms a stable mass resistant to deformation and dissolution.

However, there are some drawbacks to such compositions. If provided as a pre-mixed suspension of DBM and hydrated gelatin, the product must be stored frozen to prevent degradation of the osteoinductive capability of the DBM. Prior to use, frozen material must not only be thawed but raised above the gel transition temperature in order to yield a free-flowing paste.

Regeneration Technologies, Inc. produces a version of OSTEOFIL™ that can be stored at room temperature. This version is comprised of a mixture of DBM particles and gelatin particles. The drawback of this paste composition and method of preparation is that heated liquid and/or aggressive mixing is required to produce a uniform and free-flowing suspension (U.S. Patent Applications 20010016703, 20010037091, 20030180262).

It is conventional to store drugs, vaccines, medicaments, and solutions in a sealed vial or other container for later use. Drugs, vaccines, medicaments, and solutions may be stored in a dry or powdered form to increase the shelf life and reduce inventory space. Such dry or powdered materials are typically stored in a conventional sealed vial having a puncturable closure, such as an elastomeric stopper, and reconstituted in liquid form for later use, such as administration to a patient, by adding a diluent or solvent.

Dry materials available for reconstitution may also be stored directly in a syringe. For example, as described in U.S. Pat. No. 6,773,714 (Dunn, 2004), leuprolide acetate, a peptide drug, is lyophilized directly in a syringe prior to use. A biodegradable polymer and solvent solution is filled into another syringe. The two syringes are coupled together and the contents are drawn back and forth between the two syringes until the polymer/solvent solution and the leuprolide acetate are effectively mixed together, forming a flowable composition. The flowable composition is drawn into one syringe and the two syringes then disconnected. A needle is inserted onto the syringe containing the flowable composition and then injected through the needle into the body. Other flowable compositions are described in U.S. Pat. Nos. 5,324, 519; 4,938,763; 5,702,716; 5,744,153; and 5,990,194. None of these techniques, though, anticipate the preparation of an easily dispersible bioactive particle composition, prepared from the precipitation of a high molecular-weight polymer onto the bioactive particle, with the described characteristics in the present invention.

SUMMARY OF THE INVENTION

A. Features and Advantages of the Invention

The present invention overcomes these and other inherent deficiencies in the, prior art by providing novel bioactive particles and preparation methods for use in preparing improved therapeutic products. The described processes involve forming bioactive particles in a solution and/or microencapsulating particles, and compositions produced thereby. The process utilizes alcohol precipitation under mechanical stirring at controlled temperatures, which provides the proper forces during precipitation to control the particle growth and mixing properties. Preferential precipitation of the higher molecular weight fraction of the matrix material produces desirable final compositions with high surface area, controllable gelation, and shelf-life stability. Bioactive particles may be (1) formed in a solution to obtain a particle suspension and then (2) dried in an oven or fluid bed to control the structure of the particle or particle surface. In general, the process can be used to microencapsulate bioactive particles by suspending the drug particles in a solution including a coating material (such as a biodegradable polymer) and adding alcohol to the solution under controlled process conditions. The bioactive particle compositions produced thereby possess improved properties including, but not limited to, improved flow and syringability, controlled adhesion, stability, and/or resistance to moisture. This process, and the compositions produced, also provide significant advantages in the manufacture of bioactive particulate formulations, as well as biomedical particulate compositions, where sensitive macromolecules, such as proteins or DNA, are involved that would be degraded using more rigorous processing conditions or temperatures.

B. Summary of the Invention

The present invention provides compositions for repairing bone that comprise: bioactive particles; and a coating on the bioactive particles comprising at least one high molecular weight polymer, wherein the composition is in a form capable of repairing bone. The bioactive particles may be chosen from mineral particles, ceramic particles and processed bone particles. The processed bone particles may be derived from human, bovine, ovine or porcine sources. The processed bone particles may be derived from a demineralized bone matrix and range in size from about 100 to about 800 microns. Alternatively, the processed bone particles may comprise ground cortical and cancellous bone chips ranging in size from about 1.0 to about 3.0 millimeters. In some embodiments, one or more compositions described herein are in paste form. The paste may be prepared by contacting the bioactive particles coated with at least one high molecular weight polymer with a solution. The high molecular weight polymer may be a naturally occurring high molecular weight polymer. The high molecular weight polymer may be a synthetic polymer. The high molecular weight polymer may be chosen from gelatin, pectin, hydrogel polymers, polycarbophils, polyanhydrides, polyacrylic acids, alginates, and gums. The composition may further comprise a drug. The composition for repairing bone may comprise: bioactive particles; and a coating on the bioactive particles that may comprise at least one at least one high molecular weight polymer, wherein the composition may be in a form capable of repairing bone; wherein the bioactive particles may be derived from a demineralized bone matrix and range in size from about 100 to about 800 microns; wherein the high molecular weight polymer may be gelatin.

The present invention provides a method of preparing a composition for repairing bone comprising: providing a solution comprising at least one high molecular weight polymer; adding bioactive particles to the solution; and precipitating the at least one high molecular weight polymer, thereby forming bioactive particles coated with the at least one high molecular weight polymer. The high molecular weight polymer may be precipitated using a solvent chosen from 1-propanol, 2-propanol, ethanol, hexanol, and acetone. The method may involve drying the bioactive particles coated with the at least one high molecular weight polymer, thereby producing a granular preparation suitable for reconstitution. The bioactive particles may be dried in a convection oven, a vacuum oven, or a fluidized bed apparatus. The bioactive particles may be processed bone particles and the polymer may be gelatin ranging in amounts from about 1:2 to about 10:1 weight fraction. The present invention provides a composition for repairing bone prepared according to this method.

The present invention provides a method of repairing bone comprising: providing a dry composition comprising bioactive particles coated with at least one high molecular weight polymer; contacting the dry composition with a solution, thereby to convert the dry composition into a wet composition; and placing the wet composition in contact with a bone defect on an internal or external bone surface, wherein the wet composition may be capable of repairing bone.

BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
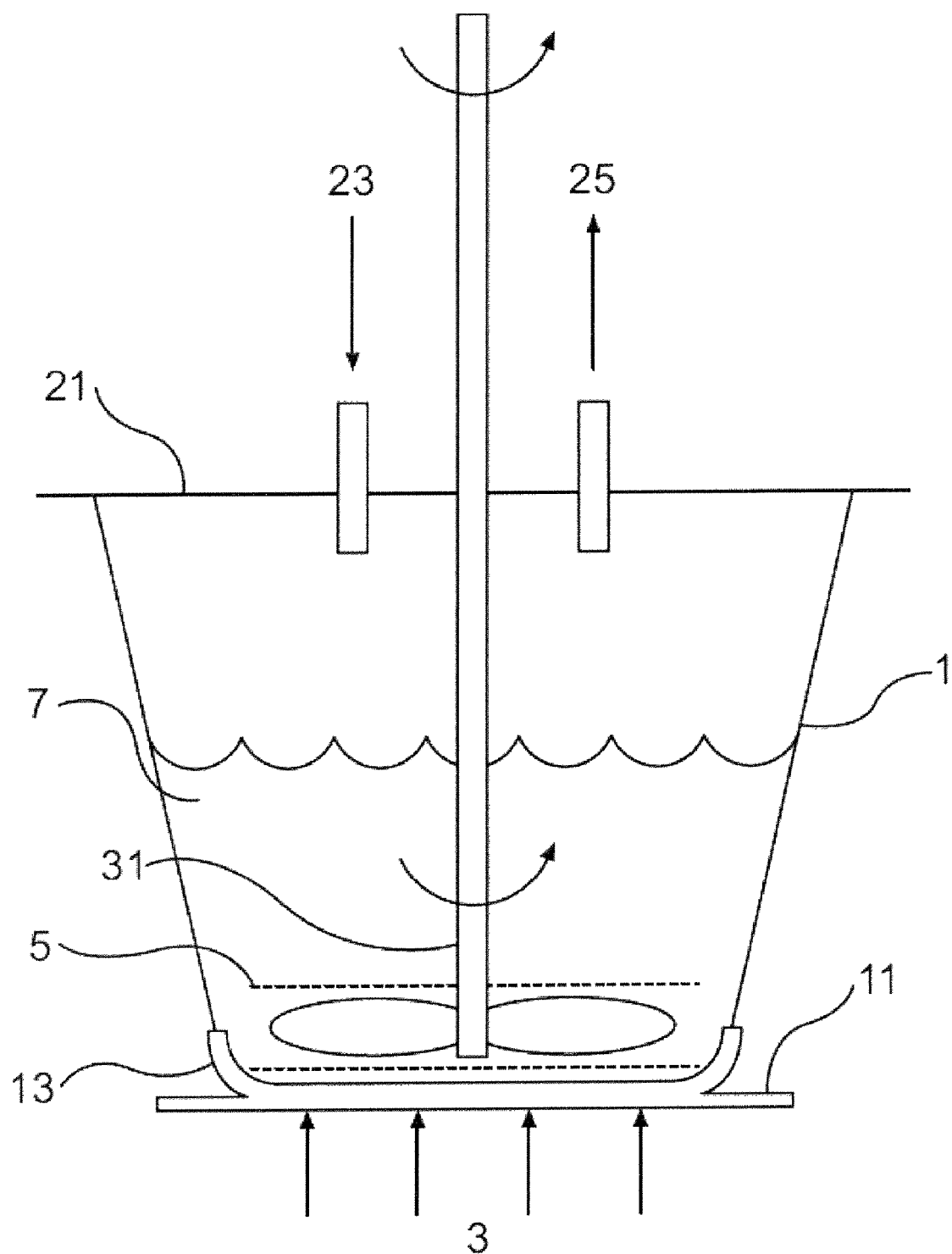
FIG. 1 is a schematic of the mixing process. A vessel, 13, which may be heated or cooled, 3, has a cover, 21, through which components of the composition may be added, 23, and through which end products and byproducts may be removed, 25. The composition may be stirred with an impeller, 31.

The invention is directed to methods of forming microencapsulated bioactive particles and wettable pastes, and the compositions produced thereby. "Bioactive particles" to be produced in accordance with this invention are typically, but not limited to, those 750 micrometers to 1.5 millimeters in size particles. Such bioactive particles and wetted paste compositions include, but are not limited to, allograft bone, xenograft bone, processed bone, natural bone substitutes, calcium salts, bioactive glasses, for human or animal use, cosmetics, as well as inert particles for which a biogels or pastes for bone void-filling or regeneration, as well as hard and soft tissue augmentation. The possibilities and combinations are numerous.

A. Compositions of Coated Bioactive Particles

The present invention relates to compositions of implantable pastes and methods for incorporating (1) mineral, ceramic, or processed bone particles as the BP and additionally (2) binders, bulking agents, excipients, and/or surface modifiers as the MM into easily wetting granular product that provides the same or improved shelf-life stability of current dry compositions but much simpler reconstitution. This is achieved by coating the component or components selected from group (1) with one or more of the components from group (2) to yield a dry, granular composition that wets easily to form a cohesive yet malleable paste.

For example, demineralized bone matrix (DBM) particles might be coated with a thin layer of gelatin and subsequently dried. The resulting dry granular composition will easily wet when an aqueous solution such as physiologic saline is added. The thin gelatin layer around each particle of DBM will absorb water from the saline and become adhesive. The coated particles will form a cohesive and malleable paste even though a) the gelatin coating may not be completely rehydrated and b) the paste may not be at a temperature above the gel transition temperature.

For use in so-called bone pastes, a variety of matrix materials have been tested including hydrogel polymers, polycarbophils, polyanhydrides, polyacrylic acids, alginates, gelatins, gums, and pectin. Adhesion may be affected by physical or mechanical bonds; secondary chemical bonds; and/or primary, ionic or covalent bonds, which can improve the adhesion of delivery system or viscosity. The disclosed method may be used to coat mineral, ceramic, and/or processed bone particles with such materials to produce an implantable composition with good shelf-life stability, ease of storage, and ease of reconstitution. Those coating materials that do not possess a gel transition temperature may lack the resistance to lavage that a gelatin based composition would possess. However, such compositions would still possess the ease and rapidity of reconstitution afforded by this method.

When delivering a non-soluble particulate material or composition to a site in the body for the purposes of promoting acceleration, delay, or enhancement of the healing process, it is desirable to use a paste. Pastes are desirable because these are easily formed to fill irregular voids or volumes, yet tend to remain where they are placed.

When the implanted material is organic or tissue-derived, long-term storage of the material becomes an issue. In the case of so-called bone pastes, the DBM in these pastes is subject to hydrolytic degradation if stored hydrated at room temperature. Frozen pastes require low-temperature freezers for transportation and storage, as well as time to thaw prior to use. Current dry compositions of pastes require aggressive mixing and warm liquids to reconstitute and, in the case of gelatin based pastes, must be maintained at a temperature above body temperature to be easily flowable.

B. Methods for Forming Coated Bioactive Particles

In the current invention, the inventors found that it is possible to produce porous compositions that wet easily and reconstitute to an implantable paste without the need of aggressive mixing. It is the object of this invention to produce such paste compositions consisting of bioactive particles of minerals, ceramics, and/or processed bone, and coating these bioactive particles with a wettable material or materials capable of forming a viscous gel upon exposure to water, such as gelatin, pectin, hydrogel polymers, polycarbophils, polyanhydrides, polyacrylic acids, alginates, and gums; with or without the inclusion of drugs, binders, wetting agents, and/or bulking agents.

One particular embodiment of this invention is to produce a dry granular composition comprised of DBM coated with gelatin in the approximate mass ratio of 8 parts DBM to 3 parts gelatin. Such a composition is reconstituted to a malleable paste by exposing a densely packed plug of the composition in the approximate mass ratio of 7 parts dry composition to 4 parts water and allowing the mixture to sit for approximately 30 seconds, or such time sufficient for the gelatin coating on the DBM particles to rehydrate. Other aqueous solutions, such as saline, sera, or whole blood, could be substituted for water.

To produce this dry composition, damp DBM particles taken at the end of the demineralization process would be assayed for water content. Once the dry mass of DBM particles is calculated by known methods, these damp DBM particles would be added to a sufficient quantity of 3% m/m gelatin solution in deionized water to produce an approximate mass ratio of 2 parts DBM to 1 part gelatin. The excess of gelatin is required because some of the gelatin will be lost during the coating process through incomplete precipitation. The gelatin/DBM suspension starts out above its gelation temperature. The suspension is agitated or rapidly stirred while a quantity of isopropanol, ethanol, and/or acetone, for example, is added slowly to the mix. A simple schematic of a mixing apparatus is depicted in FIG. 1. Low-frequency sonication may be used in addition to stirring, as described in PCT application WO 03/090717. The isopropanol, ethanol, and/or acetone acts as a non solvent for the gelatin in solution. Similarly, a metal ion complexing agent, such as zinc, or pH shift may be used to precipitated the gelatin. The quantity of nonsolvent needed to drive gelatin out of solution depends on the non-solvent chosen, its temperature, and the concentration of gelatin in solution.

It can be observed by those skilled in the art that the cloudiness of the supernatant during the coating process is a result of less than all of the gelatin coming out of the solution at once. The least soluble (generally higher molecular weight) traction of gelatin will be precipitated first. Thus, this process and composition differs from that taught by Scheicher (U.S. Pat. No. 4,191,747) and others in so far as not only are the particles pre-coated with gelatin prior to creating an implantable paste, but the resulting intermediate composition is comprised of DBM suspended in gelatin of higher average molecular weight than other methods, because of how the gelatin was attached onto the surface of the DBM particles. The resulting compositon is easily dried and demonstrates improved stability and wettability compared to other compositions.

Once sufficient gelatin has been deposited onto the DBM particles the mixer can be stopped and the supernatant decanted. In the case of isopropanol used as the non-solvent, a volume is chilled to 15 degrees Celsius and approximately 5 parts added to 1 part initial gelatin solution as a volume ratio and agitated for about 3 minutes. The remaining material is filtered through a 270 mesh seive and washed again in isopropanol with agitation for about 2 minutes. The resulting particulate mass is then dried overnight in an oven at 35 degrees Celsius, yielding a granular powder that wets easily to form a cohesive, malleable paste.

This granular composition can be loaded into appropriate containers and sterilized via ionizing radiation (X-ray, e-beam, or gamma). It will be recognized by one skilled in the art that the amount of material required for the desired effect on administration will, of course, vary with the composition and the nature and severity of the condition and size of the person or animal undergoing treatment, and is ultimately at the discretion of the physician.

While various embodiments of the present invention have been described above, it should be understood that they have been presented by way of example only, and not limitation. The present invention is not limited to the described compositions and methods, nor is it limited to a particular composition or material, nor is the present invention limited to a particular scale or batch size of production. Thus, the breadth and scope of the present invention should not be limited by any of the above-described exemplary embodiments, but should be defined only in accordance with the following claims and their equivalents.

C. Uses for Coated Bioactive Particals

Bioactive particles coated with matrix material or matrix materials may be used to produce easily reconstituted and malleable pastes. Such compositions may be placed in contact with an internal or external bone surface for the purposes including, but not limited to, void filling, e.g. inducing or conducting the regrowth of bony tissue in a surgically or traumatically induced void in boney tissue. Such pastes may also be used to form drug depots, e.g. bioactive particles with chemotherapy agents may be injected into a surgically induced void from which cancerous tissue was removed.

D. Examples

The following examples are included to demonstrate example embodiments of the invention. It should be appreciated by those of skill in the art that the techniques disclosed in the examples which follow represent techniques discovered by the inventors to function well in the practice of the invention, and thus can be considered to constitute relevant examples for its practice. However, those of skill in the art should, in light of the present disclosure, appreciate that many changes can be made in the specific embodiments which are disclosed and still obtain a like or similar result without departing from the spirit and scope of the invention.

Example 1

A solution of porcine gelatin (12 g) in water (388 g) was stirred in a polypropylene pitcher using a Lightnin Mixer with a two-blade impeller. To this was added bovine tendon collagen (15.8 g). To this was added a total of 1900 ml of isopropyl alcohol. After precipitate formed, the stirring was stopped and the particles were allowed to settle. Supernatant was decanted and the particulate material was rinsed with 300 ml of isopropyl alcohol. Decanting and rinsing were repeated again. After final decant, the curd-like particles were dried at room temperature under vacuum overnight. A total of 22.1 g of finely divided dry curd-like particles were collected. Moisture content, as determined by loss on heating, was 7.8% mass/mass. Approximately 1.4 g was placed in a 10 ml syringe and wetted with 1 ml saline, easily syringable after reconstitution.

Example 2

A solution of porcine gelatin (6 g) in water (194 g) was stirred in a polypropylene pitcher using a Lightnin Mixer with a two-blade impeller. To this was added calcium sulfate dihydrate particles (12.35 g; sieved to 1-3 mm size range). To this was added a total of 900 ml of isopropyl alcohol. After precipitate formed, the stirring was stopped and the particles were allowed to settle. Supernatant was decanted and the particulate material was rinsed with 200 ml of isopropyl alcohol. Decanting and rinsing were repeated again. After final decant, the curd-like particles were dried at room temperature under vacuum for 5.5 hours. A total of 22.1 g of finely divided dry curd-like particles were collected. Moisture content, as determined by loss on heating, was 15.8% mass/mass.

Example 3

A solution of porcine gelatin (3 g) in water (100 g) was stirred in a 600 ml pyrex beaker using a magnetic stir bar. To this was added Bioglass® 45S5 bioactive glass particles (6.0 g; sieved to 90 to 710 micron size range). To this was added a total of 350 ml of isopropyl alcohol. After precipitate formed, the stirring was stopped and the particles were allowed to settle. Supernatant was decanted and the particulate material was rinsed with 150 ml of isopropyl alcohol. Decanting and rinsing were repeated again. After final decant, the curd-like particles were dried at room temperature under vacuum overnight. A total of 8.3 g of finely divided dry curd-like particles were collected. Moisture content, as determined by loss on heating, was 6.1% mass/mass.

Figure 2A:
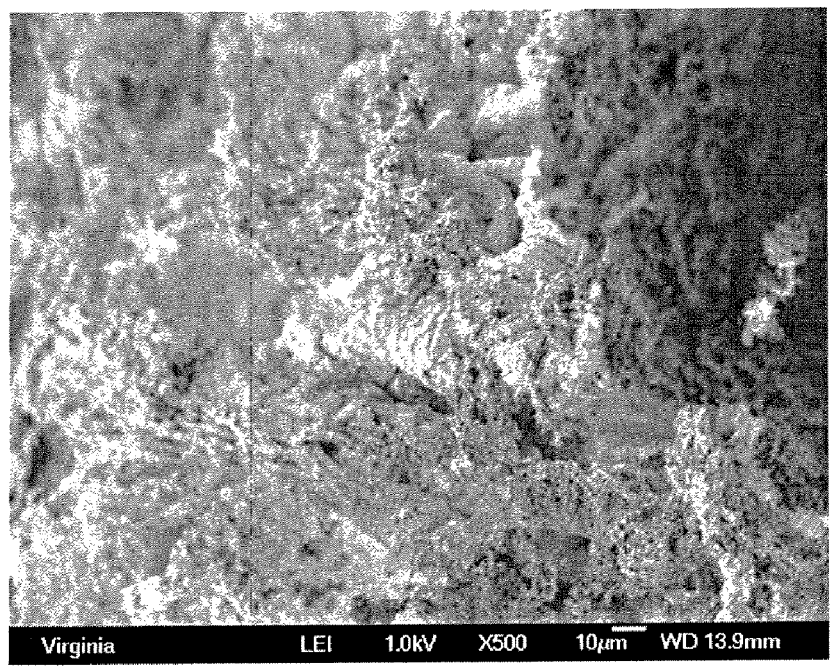
FIG. 2A is a scanning electron micrograph of Bioglass® 45S5 bioactive glass particles coated with porcine gelatin at 500 times magnification.
Figure 2B:
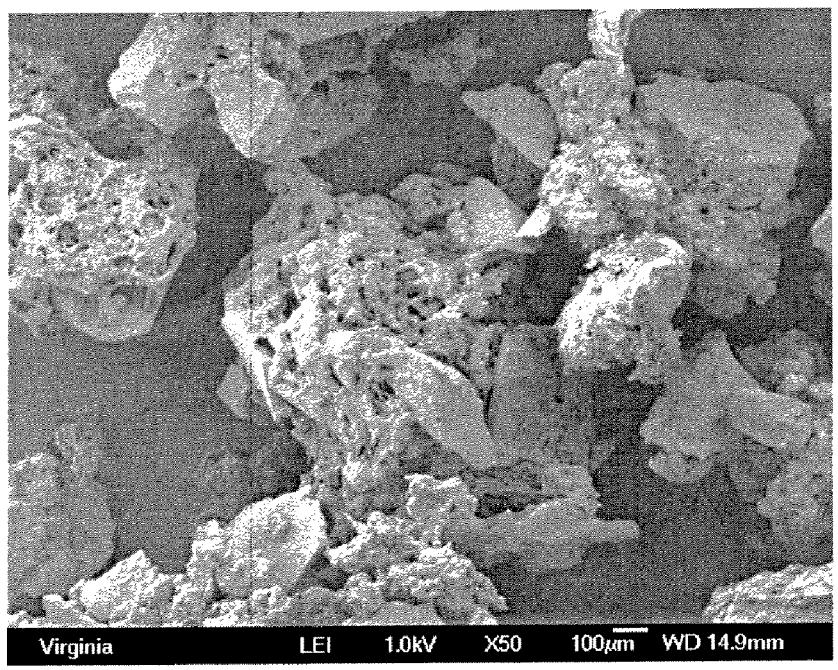
FIG. 2B is a scanning electron micrograph of Bioglass® 45S5 bioactive glass particles coated with porcine gelatin at 50 times magnification.
Figure 5A:
FIG. 5A is an x-ray radiograph, taken at day 28, of coated bovine bone chips implanted in the mouse. The bright area indicates mineralization is still present.
Figure 5B:
FIG. 5B is an x-ray radiograph, taken at day 28, of coated bioactive glass particles implanted in the mouse. The bright area indicates mineralization is still present.

The particles are shown in FIG. 2A and B and appeared several hundred microns in size, with regions of incomplete gelatin coating attached to the surface. The particles mixed easily in a plastic weighboat to form a sticky clump of putty-like material. Approximately 1.7 g was placed in a 10 ml syringe and wetted with 1 ml saline, easily syringable after reconstitution. Samples were placed into leg muscle ectopic sites of athymic mice and 28 day radiographs are shown in FIG. 5A, demonstrating sites of mineral deposits. Additional samples were packed into syringes and sterilized by gamma-irradiation. Further, reconstituted samples were injected into critical-size drilled defects in rabbits and demonstrated osteoconductive responses by radiography.

Example 4

Figure 3A:
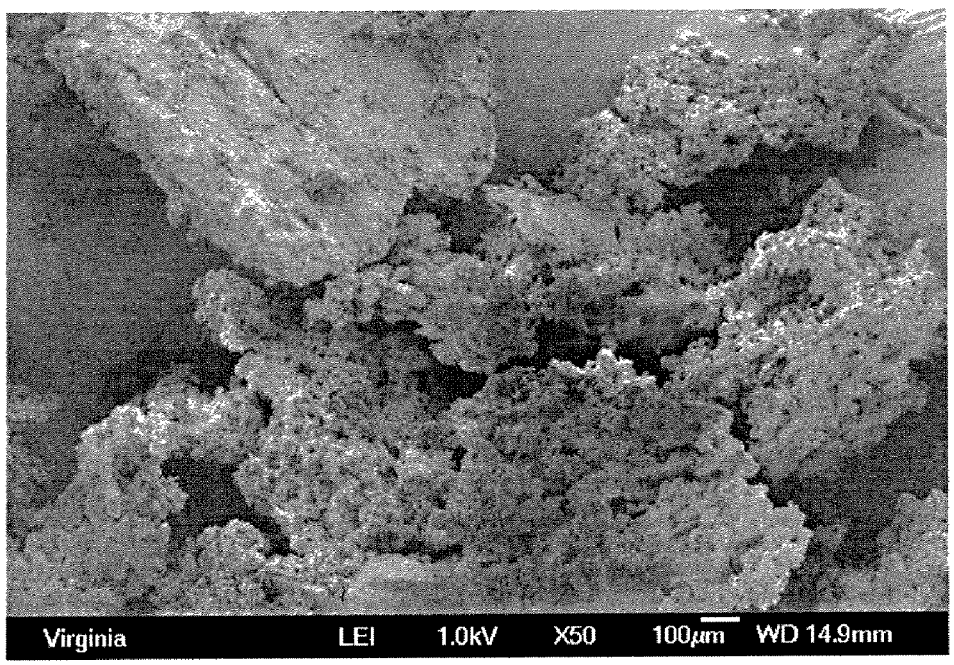
FIG. 3A is a scanning electron micrograph of processed bovine cortical bone chips coated with porcine gelatin at 50 times magnification.

A solution of porcine gelatin (34.5 g) in water (1,115 g) was stirred in a polypropylene pitcher using a Lightnin Mixer with a two-blade impeller. To this was added demineralized bovine bone (bovine DBM) suspension (35 g) taken right after the acid neutralization step (i.e. 53.5 g moist demineralized bone). To this was added a total of 3000 ml of isopropyl alcohol. After precipitate formed, the stirring was stopped and the particles were allowed to settle. Supernatant was decanted and the particulate material was rinsed with ca. 400 ml of isopropyl alcohol. Decanting and rinsing were repeated two more times. After final decant, the particulate curds were dried at room temperature under vacuum for 17 hours. After sieving, 96.5 g of spongy dry curd-like particles were obtained with approximately 35% moisture content. The particles are shown in FIG. 3A and appeared several hundred microns in size with a roughened surface indicating a gelatin coating. Approximately 1.3 g was placed in a 10 ml syringe and wetted with 0.8 ml saline and 1 ml rat blood, both samples easily syringable after reconstitution.

In addition, the molecular weight of (A) autoclaved gelatin starting solution (1% in water) was compared to (B) gelatin diluted (1%) from the above Example as well as (C) Example 3. Size Exclusion Chromotography (SEC) chromatograms, including the molecular weight marker (D) shows thyroglobulin (bovine, MW 670,000) at 6.919 minutes, g-globulin (bovine, MW=158,000) at 8.101 minutes, ovalbumin (chicken, MW 44,000) at 9.108 minutes, myoglobin (horse, MW=17,000) at 11.212 minutes, and vitamin B12 (MW 1,350) at 14.440 minutes. These SEC profiles display clearly that the described method selectively coats the bioactive particles with the high molecular weight fraction of the polymer, in this case gelatin, and the low molecular weight fraction stays in solution and is decanted off before drying.

Example 5

Figure 3B:
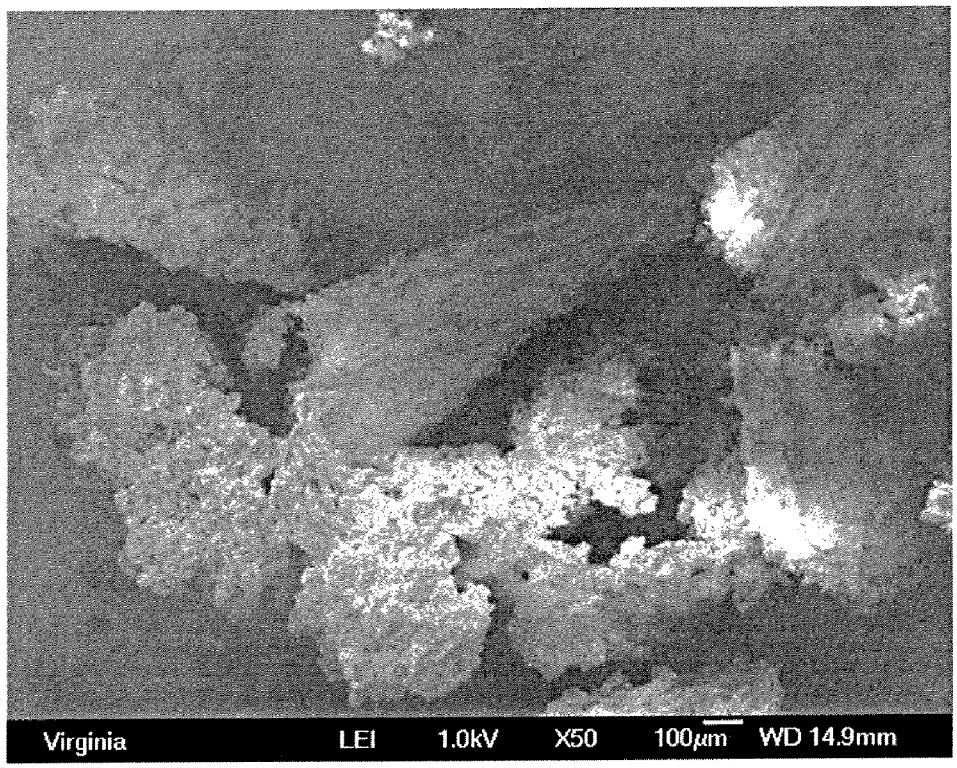
FIG. 3B is a scanning electron micrograph of demineralized bone matrix coated with porcine gelatin at 50 times magnification.
Figure 4A:
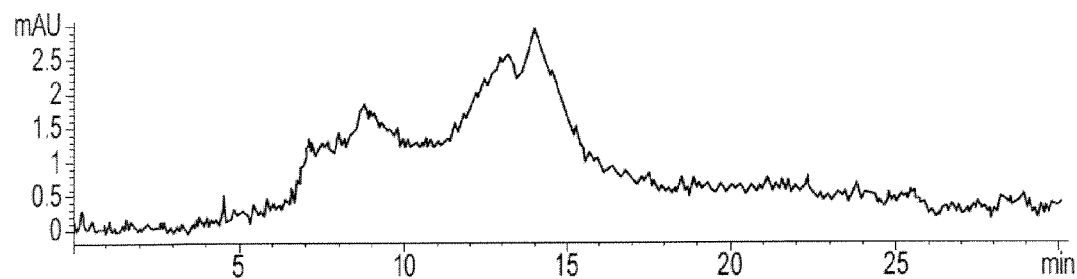
FIG. 4 is an example of size exclusion chromatography spectra for the porcine gelatin at different stages of the process. The top trace (A) shows the initial autoclaved porcine gelatin solution before coating. The top middle trace (B) is from gelatin found on the coated particles from Example 4. The bottom middle trace (C) is from gelatin found on the coated particles from Example 3. The bottom trace (D) is for the molecular weight standards used to calibrate the runs. The shifting to the left of the dominant peaks seen in the two middle traces relative to the top and bottom traces indicate the coating process excludes lower molecular weight fractions of the gelatin.
Figure 4B:
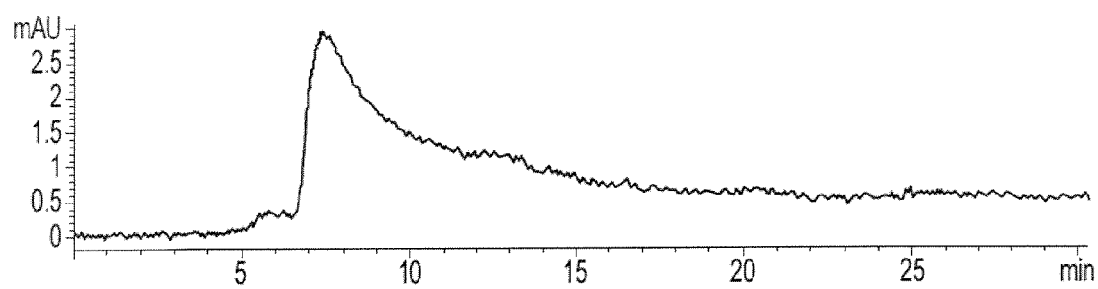
Figure 4C:
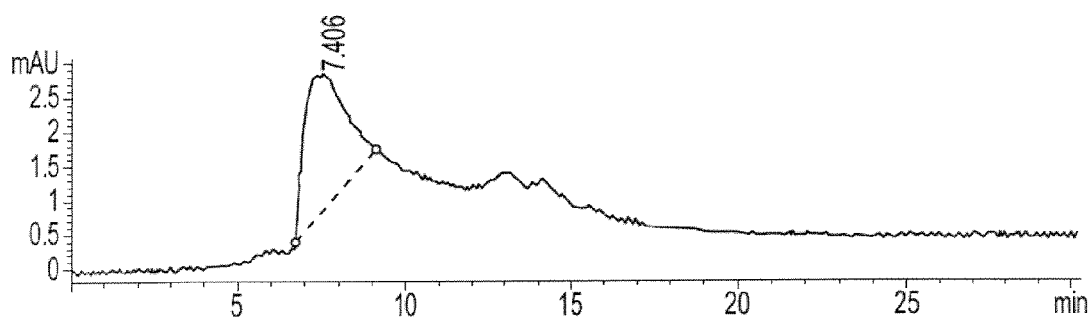
Figure 4D:
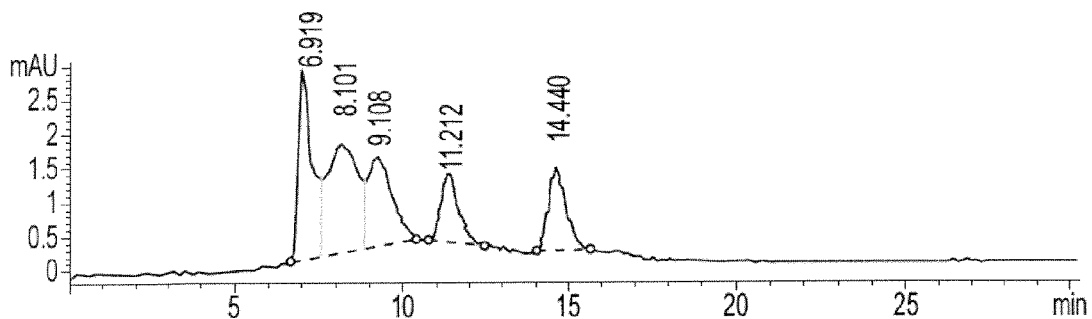

A solution of porcine gelatin (25 g) in water (808 g) was stirred in a polypropylene pitcher using a Lightnin Mixer with a two-blade impeller. To this was added ground bovine cortical bone particles (50 g; cleaned; moist; sieved to 150-1,000 micron size range). To this was added a total of 2400 ml of isopropyl alcohol. After precipitate formed, the stirring was stopped and the particles were allowed to settle. Supernatant was decanted and the particulate material was rinsed with 600 ml of isopropyl alcohol. Decanting and rinsing were repeated two more times. After final decant, the curd-like particles were dried at room temperature under vacuum overnight. A total of 71 g of dry curd-like particles were collected. The particles are shown in FIG. 3B and appeared several hundred microns in size and gelled upon mixing with saline.

Example 6

A solution of hyaluronic acid (4.5 g) in water (300 g) was stirred in a polypropylene pitcher using a Lightnin Mixer with a two-blade impeller. To this was added demineralized bovine cortical bone (11.2 g). To this was added a total of 600 ml of isopropyl alcohol. After precipitate formed, the stirring was stopped and the particles were allowed to settle. Supernatant was decanted and the particulate material was rinsed with 300 ml of isopropyl alcohol. Decanting and rinsing were repeated again. After final decant, the curd-like particles were dried at room temperature under vacuum overnight. Large clumped curd-like particles were produced; some clear indicating hyaluronic acid was not thoroughly dissolved.

Example 7

A solution of 100,000 molecular weight polyethylene oxide (ca 2.5 g) in water (50 ml) was stirred for 30 seconds after the addition of Bioglass® bioactive glass (2.5 g; sieved to 90-710 micron size range). To this was added a solution of isopropyl alcohol and hexanol (120 ml, 1:5 ratio) while stirring for another minute. Solution was placed in the freezer (−5 degrees C.) under stirring where precipitate formed after 1 hour. Supernatant was decanted and the particulate material was rinsed with 100% hexanol. Decanting and rinsing were repeated again. After final decant, the curd-like particles were dried at room temperature under vacuum overnight.

Example 8

A solution of porcine gelatin (3 g) and polyhexamethylene biguanide (PHMB, a biguanide antimicrobial, 100 mg) in water (100 g) was stirred in a 600 ml pyrex beaker using a magnetic stir bar. To this was added Bioglass® 45S5 bioactive glass particles (6.0 g; sieved to 90 to 710 micron size range). To this was added a total of 350 ml of isopropyl alcohol. After precipitate formed, the stirring was stopped and the particles were allowed to settle. Supernatant was decanted and the particulate material was rinsed with 150 ml of isopropyl alcohol. Decanting and rinsing were repeated again. After final decant, the curd-like particles were dried at room temperature under vacuum overnight. A total of approximately 8 g of finely divided dry curd-like particles were collected. Moisture content, as determined by loss on heating, was similar to Example 3 above and PHMB content, analyzed by HPLC, was approximately 1%. After reconstitution, the antimicrobial slow-releasing paste could be used to prevent infection for several days following placement in the wound. Similar drug-releasing systems incorporating drugs and/or bioactive proteins could be prepared in a similar fashion by mixing during the precipitation step or after the particles are dried. Finally, a drug or bioactive protein could also be introduced in the reconstitution fluid to produce a homogenous mixture.

Example 9

A solution of porcine gelatin (87 g) in water (2,813 g) was stirred in a stainless steel bowl using a air-powered stirrer with a two-blade impeller. To this was added Bioglass® 45S5 bioactive glass particles (174 g). To this was added a total of 9,000 ml of isopropyl alcohol. After precipitate formed, the stirring was stopped and the particles were allowed to settle. Supernatant was decanted and the particulate material was rinsed with ca. 3,000 ml of isopropyl alcohol. Decanting and rinsing were repeated two more times. After final decant, the particulate curds were dried in a Glatt Uni-Glatt fluid bed dryer at 35° C. for 1 hour. After sieving, 230 g of dense dry curd-like particles were obtained. Approximately 2.6 g was placed in a 10 ml syringe and wetted with 2.0 ml saline, both samples easily syringable after reconstitution.

CITED DOCUMENTS

1. Wironen, J. F. and Grooms, J. M., "Bone paste", U.S. Pat. Applic. 20020098222, submitted Mar. 13, 1997.
2. Wironen, J. F., "Thermally sterilized bone paste", U.S. Pat. Applic. 20020018796, submitted Jan. 28, 1998.
3. Wironen, J., Felton, P., and Jaw, R. "Bone paste subjected to irradiative and thermal Treatment", U.S. Pat. Applic. 20020076429, submitted Sep. 16, 1998.
4. Scheicher, H., "Corrective agent for the covering and/or filling of bone defects, method for the preparation of same and method of using the same", U.S. Pat. No. 4,191,747, issued Mar. 4, 1980.
5. Wironen, J., Kao, P., and Bernhardt, A., "System for reconstituting pastes and methods of using same", U.S. Pat. Applic. 20010016703, submitted Dec. 29, 2000.
6. Wironen, J., and Walpole, M., "System for reconstituting pastes and methods of using same", U.S. Pat. Applic. 20010037091, submitted Nov. 1, 2001
7. Wironen, J., Kao, P., and Bernhardt, A., "System for reconstituting pastes and methods of using same", U.S. Pat. Applic. 20030180262, submitted Oct. 11, 2001.
8. Talton, J. and McConville, C, "Process for forming and modifying particles and compositions produced thereby", PCT application WO 03/090717, filed Apr. 23, 2002.

What is claimed is:
1. A method of preparing a dry, granular composition for repairing bone comprising:
(a) providing a solution comprising at least one high molecular weight biodegradable polymer;
(b) adding bioactive particles consisting of bioactive glass to the solution; and
(c) precipitating the at least one high molecular weight biodegradable polymer, thereby forming bioactive particles individually microencapsulated coated with a coating comprising the at least one high molecular weight biodegradable polymer, wherein the mass ratio of the bioactive particles to the coating ranges from about 1:2 to about 10:1, and the dry, granular composition when wetted forms a syringeable paste capable of repairing bone, and is prepared by contacting the microencapsulated bioactive particles with a solution.

2. The method of claim 1, wherein the at least one high molecular weight biodegradable polymer is precipitated using a solvent chosen from 1-propanol, 2-propanol, ethanol, hexanol, and acetone.

3. The method of claim 1, further comprising the step of drying the individually microencapsulated bioactive particles, thereby to produce a granular preparation suitable for reconstitution.

4. The method of claim 1, wherein the bioactive particles are dried in a convection oven, a vacuum oven, or a fluidized bed apparatus.

5. The method of claim 1, wherein the biodegradable polymer is gelatin.

6. A composition for repairing bone prepared according to the method of claim 1.

7. The method of claim 1, wherein the solution comprises at least one or more drugs, at least one or more bioactive proteins, and/or combinations thereof.

8. A method of preparing a dry, granular composition for repairing bone, comprising:
   (a) providing a solution comprising at least one biodegradable polymer;
   (b) adding bioactive particles comprising bioactive glass to the solution; and
   (c) precipitating the at least one biodegradable polymer, thereby forming bioactive particles individually microencapsulated with a coating comprising the at least one biodegradable polymer, wherein the mass ratio of the bioactive particles to the coating ranges from about 1:2 to about 10:1,
   the dry, granular composition when wetted forms a syringeable paste capable of repairing bone, and the bioactive particles do not include particles derived from bone.

9. The method of claim 8, wherein the biodegradable polymer is gelatin.

10. The method of claim 8, wherein the bioactive particles range in size from about 750 microns to about 1.5 millimeters.

11. The method of claim 8, wherein the dry, granular composition when wetted forms a syringeable paste at a temperature below the gel transition temperature of the biodegradable polymer.

12. The method of claim 8, wherein the solution comprises at least one or more drugs, at least one or more bioactive proteins, and/or combinations thereof.

13. The method of claim 8, wherein the at least one biodegradable polymer is precipitated using a solvent chosen from 1-propanol, 2-propanol, ethanol, hexanol, and acetone.

14. The method of claim 13, wherein the solvent comprises at least one or more drugs, at least one or more bioactive proteins, and/or combinations thereof.

15. The method of claim 8, wherein the syringeable paste is prepared by contacting the individually microencapsulated bioactive particles with a solution.

16. The method of claim 15, wherein the solution comprises at least one or more drugs, at least one or more bioactive proteins, and/or combinations thereof.

17. A method of preparing a dry, granular composition for repairing bone, comprising:
   (a) providing a solution comprising at least one biodegradable polymer;
   (b) adding bioactive particles consisting of bioactive glass to the solution; and
   (c) precipitating the at least one biodegradable polymer, thereby forming bioactive particles individually microencapsulated with a coating comprising the at least one biodegradable polymer, wherein the mass ratio of the bioactive particles to the coating ranges from about 1:2 to about 10:1, wherein the dry, granular composition when wetted forms a syringeable paste capable of repairing bone, and said at least one biodegradable polymer comprises gelatin.

18. The method of claim 17, wherein the dry, granular composition when wetted forms a syringeable paste at a temperature below the gel transition temperature of gelatin.

19. The method of claim 17, wherein the dry, granular composition is osteoinductive.

20. The method of claim 17, wherein the gelatin is porcine gelatin.

21. The method of claim 17, wherein the individually microencapsulated particles range in size from about 750 microns to about 1.5 millimeters.

22. The method of claim 17, wherein the syringeable paste is prepared by contacting the individually microencapsulated bioactive particles with a solution.

23. The method of claim 17, wherein the solution comprises at least one or more drugs, at least one or more bioactive proteins, and/or combinations thereof.

24. The method of claim 17, wherein the at least one biodegradable polymer is precipitated using a solvent chosen from 1-propanol, 2-propanol, ethanol, hexanol, and acetone.

\* \* \* \* \*